United States Patent
Chen et al.

(10) Patent No.: US 12,123,821 B2
(45) Date of Patent: Oct. 22, 2024

(54) COMBINED APPARATUS FOR EXPERIMENTATION ON DIFFERENT STORAGE MODES OF CARBON DIOXIDE AND METHOD THEREOF

(71) Applicant: China University of Petroleum (Beijing), Beijing (CN)

(72) Inventors: Hao Chen, Beijing (CN); Xiliang Liu, Beijing (CN); Weiming Cheng, Beijing (CN); Mingsheng Zuo, Beijing (CN); Borui Li, Beijing (CN); Baoxi Yang, Beijing (CN); Yi Wu, Beijing (CN); Haipeng Liu, Beijing (CN); Xinyu Qi, Beijing (CN); Feng Luo, Beijing (CN); Linxi Yang, Beijing (CN); Wen Liu, Beijing (CN); Pengbo Li, Beijing (CN)

(73) Assignee: CHINA UNIVERSITY OF PETROLEUM (BEIJING), Beijing (CN)

( * ) Notice: Subject to any disclaimer, the term of this patent is extended or adjusted under 35 U.S.C. 154(b) by 0 days.

(21) Appl. No.: 18/537,463

(22) Filed: Dec. 12, 2023

(65) Prior Publication Data
US 2024/0264065 A1 Aug. 8, 2024

(30) Foreign Application Priority Data
Feb. 6, 2023 (CN) .......................... 202310132938.8

(51) Int. Cl.
*G01N 15/08* (2006.01)
*G01N 33/24* (2006.01)
*E21B 43/16* (2006.01)

(52) U.S. Cl.
CPC ......... *G01N 15/0893* (2013.01); *G01N 33/24* (2013.01); *E21B 43/164* (2013.01)

(58) Field of Classification Search
CPC ...... G01N 15/00; G01N 15/08; G01N 15/088; G01N 15/0893; G01N 33/24; E21B 43/16; E21B 43/164
See application file for complete search history.

(56) References Cited

U.S. PATENT DOCUMENTS

| 2013/0064604 A1 | 3/2013 | Han et al. |
| 2022/0381122 A1 | 12/2022 | Pope et al. |

FOREIGN PATENT DOCUMENTS

| CN | 202102631 | 1/2012 |
| CN | 202102631 U | 1/2012 |

(Continued)

OTHER PUBLICATIONS

Machine Translation of CN-111189994-A (Year: 2020).*
(Continued)

*Primary Examiner* — Nguyen Q. Ha
(74) *Attorney, Agent, or Firm* — Pilloff Passino & Cosenza LLP; Rachel K. Pilloff; Sean A. Passino (57) ABSTRACT

The present disclosure discloses a combined apparatus for experimentation on different storage modes of carbon dioxide, which comprises a displacement device, a storage reaction device and a measuring device, wherein the displacement device comprises a displacement pump, and an intermediate oil-water container and an intermediate carbon dioxide container that are arranged in parallel, the displacement pump is connected to a first end of the parallel connection of the intermediate oil-water container and the intermediate carbon dioxide container, and an inlet end of the storage reaction device is connected to a second end of the parallel connection of the intermediate oil-water container and the intermediate carbon dioxide container; the measuring device comprises a weigher, a first pressure detector, a gas-liquid separator, a gas meter and a mineral analyzer, wherein the first pressure detector is arranged in (Continued)

the intermediate oil-water container, and the gas-liquid separator is connected to the outlet end of the storage reaction device. Thus, the storage amount of carbon dioxide in different storage modes can be evaluated by means of a single apparatus. Compared with the prior art in which different storage experiments are performed separately.

9 Claims, 4 Drawing Sheets

(56) References Cited

FOREIGN PATENT DOCUMENTS

| CN | 105424729 A | | 3/2016 | |
| CN | 110578500 | | 12/2019 | |
| CN | 110578500 A | | 12/2019 | |
| CN | 111189994 A | * | 5/2020 | ......... G01N 15/0826 |
| CN | 210465311 | | 5/2020 | |
| CN | 210465311 U | | 5/2020 | |
| CN | 112459760 A | * | 3/2021 | ........... E21B 43/164 |
| CN | 113218821 A | | 8/2021 | |
| CN | 113863904 A | | 12/2021 | |
| CN | 114544463 A | | 5/2022 | |
| CN | 114577837 A | | 6/2022 | |
| CN | 115078102 A | | 9/2022 | |
| CN | 115144298 A | | 10/2022 | |
| KR | 101575002 B1 | | 12/2015 | |
| WO | 2016088002 A1 | | 6/2016 | |

OTHER PUBLICATIONS

Machine Translation of CN-112459760-A (Year: 2021).*
Hao Yongmao et al., "Research on the microscopic distribution characteristics and storage capacity of CO2 with different displacement methods," Natural Gas Geoscience, Jun. 2017, pp. 846-851, vol. 28, No. 6.
Notice of the First Office Action for China Application No. 202310132938.8, mailed Dec. 23, 2023.
Notification to Grant Patent for China Application No. 202310132938.8, mailed Jan. 22, 2024.
First Search Report for China Application No. 202310132938.8, dated Dec. 19, 2023.
Supplementary Search Report for China Application No. 202310132938.8, dated Jan. 16, 2024.
Yong-Mao et al., "Research on the microscopic distribution characteristics and storage capacity of CO2 with different displacement methods," Journal of Natural Gas Geoscience, vol. 28, No. 6, Jun. 2017, pp. 846-851.

* cited by examiner

COMBINED APPARATUS FOR EXPERIMENTATION ON DIFFERENT STORAGE MODES OF CARBON DIOXIDE AND METHOD THEREOF

CROSS-REFERENCE TO RELATED APPLICATION

This application claims the benefit of Chinese Patent Application No. 202310132938.8 filed on Feb. 6, 2023, which is hereby incorporated herein by reference in its entirety.

FIELD

The present disclosure belongs to the technical field of carbon dioxide storage, in particular, relates to a combined apparatus for experimentation on different storage modes of carbon dioxide and a method thereof.

BACKGROUND

With the advances in stimulation techniques such as horizontal wells and volume fracturing, effective exploitation of tight oil and gas resources has been realized. However, owing to the rapid depletion of crude oil in natural fractures and the slow replenishment of crude oil in the matrix, it is difficult to achieve sustainable exploitation of tight oil reservoirs. Supercritical carbon dioxide can achieve effects such as crude oil swelling, reduction of the filtration resistance of crude oil, promotion of wetting inversion of reservoir pore wall surfaces, widened pore canal diameter and pore throat dredging, etc. Enhancing oil recovery by injecting carbon dioxide has become the most promising means for increasing the yield in the late stage of development of depleted tight reservoirs, and is a win-win technique for increasing the yield of crude oil and storing greenhouse gases. Under the background of "peak carbon dioxide emissions and carbon neutrality", how to effectively reduce carbon dioxide emissions is a frontier problem to be solved urgently.

At present, the most feasible technology is the integrated carbon capture, utilization and storage (CCUS) technology. As ideal places for carbon storage and increasing the yield of oil, tight reservoirs have received more and more attention in recent years. The process of carbon dioxide storage in tight reservoirs is complex, and the storage mechanism mainly includes structural trapping, solubility trapping, sorption trapping and mineral trapping, etc. In the prior art, only solubility trapping and mineral trapping are calculated, and storage experiments are performed separately by means of separate systems and apparatuses. Therefore, the storage experiments involve complex experimental steps, numerous manual operating procedures. Consequently, the experimental results can't reflect the true carbon dioxide storage situation, and the accuracy and efficiency of the experiments are low.

SUMMARY

In view of the above-mentioned defects or drawbacks in the prior art, the present disclosure provides a combined apparatus for experimentation on different storage modes of carbon dioxide intended to solve the technical problems that the storage experiments are performed separately by means of separate systems and apparatuses, the experimental steps are complex, and many manual operating procedures are involved, which lead to the facts that the experimental result can't reflect the real storage situation of carbon dioxide, and the accuracy and efficiency of the experiments are low.

In order to attain the above-mentioned object, the present disclosure provides a combined apparatus for experimentation of different storage modes of carbon dioxide, which comprises a displacement device, a storage reaction device, and a measuring device, wherein the displacement device comprises a displacement pump, and an intermediate water-oil container and an intermediate carbon dioxide container that are in parallel connection, and the displacement pump is connected to a first end of the parallel connection of the intermediate water-oil container and the intermediate carbon dioxide container and used for displacing a displacement medium in the intermediate water-oil container and/or the intermediate carbon dioxide container; the storage reaction device has an inlet end connected to a second end of the parallel connection of the intermediate water-oil container and the intermediate carbon dioxide container and is used for performing storage experiments on an experimental rock core therein; and the measuring device comprises a weigher, a first pressure detector, a gas-liquid separator, a gas meter and a mineral analyzer, wherein the first pressure detector is arranged in the intermediate water-oil container, the gas-liquid separator is connected to the outlet end of the storage reaction device, the gas meter is used for detecting the gas separated by the gas-liquid separator, the weigher is used for weighing the weight of the experimental rock core, and the mineral analyzer is used for detecting the carbon content in the experimental rock core.

In an embodiment of the present disclosure, the intermediate water-oil container comprises a formation water container and a crude oil container, wherein the formation water container, the crude oil container and the intermediate carbon dioxide container are arranged in parallel, two first pressure detectors are provided and arranged in the formation water container and the crude oil container respectively, the front ends of the formation water container, the crude oil container and the intermediate carbon dioxide container are provided with a first valve respectively, and the rear ends of the formation water container, the crude oil container and the intermediate carbon dioxide container are provided with a second valve respectively.

In an embodiment of the present disclosure, the storage reaction device comprises a rock core holder and a second pressure detector, wherein the experimental rock core is held in the rock core holder, an inlet end of the rock core holder is connected to the second end of the parallel connection of the intermediate water-oil container and the intermediate carbon dioxide container, and the gas-liquid separator is connected to an outlet end of the rock core holder.

In an embodiment of the present disclosure, the storage reaction device further comprises a confining pressure pump connected to the rock core holder.

In an embodiment of the present disclosure, the gas-liquid separator comprises a gas-liquid separation cylinder, a gas-liquid output pipe and an exhaust pipe, wherein an inlet end of the gas-liquid output pipe is connected to the outlet end of the storage reaction device, an outlet end of the gas-liquid output pipe extends into the gas-liquid separation cylinder, an inlet end of the exhaust pipe extends into the gas-liquid separation cylinder, and an outlet end of the exhaust pipe is connected to the gas meter.

To attain the above-mentioned object, the present disclosure provides a method for experimentation on different storage modes of carbon dioxide using the combined apparatus for experimentation on different storage modes of carbon dioxide described above, comprising a method for experimentation on solubility trapping of carbon dioxide in a first experimental rock core, which comprises:

controlling the displacement pump to inject carbon dioxide to be dissolved into the formation water container;

controlling the displacement pump to inject carbon dioxide to be dissolved into the crude oil container, acquiring pressure detection data of the first pressure detectors in the formation water container and the crude oil container respectively;

obtaining a first solubility of carbon dioxide in the formation water and a second solubility of carbon dioxide in the crude oil respectively according to the pressure detection data;

controlling the displacement pump to displace the formation water with dissolved carbon dioxide in the formation water container to the storage reaction device for a water saturation operation;

measuring the weight of saturated water in the first experimental rock core after the water saturation operation;

controlling the displacement pump to displace the crude oil with dissolved carbon dioxide in the crude oil container to the storage reaction device for an oil saturation operation;

measuring the weight of saturated oil in the first experimental rock core after the oil saturation operation; and performing calculations according to the initial weight of the first experimental rock core, the density of the formation water, the density of the crude oil, the first solubility, the second solubility, the weight of the saturated water and the weight of the saturated oil, to obtain the storage amount of carbon dioxide in the first experimental rock core in the solubility trapping experiment.

In an embodiment of the present disclosure, the combined apparatus for experimentation on different storage modes of carbon dioxide further comprises a carbon dioxide adsorption instrument, which is used for performing a sorption trapping experiment on a second experimental rock core.

In an embodiment of the present disclosure, the method for experimentation on different storage modes of carbon dioxide further comprises a method for experimentation on sorption trapping of carbon dioxide in a second experimental rock core, which comprises:

acquiring the initial mass of a second experimental rock core measured by the weigher, wherein the physical properties of the second experimental rock core are the same as those of the first experimental rock core;

acquiring the adsorption amount of carbon dioxide in the second experimental rock core measured with the carbon dioxide adsorption instrument in a sorption trapping experiment; and performing calculations according to the initial mass of the first experimental rock core, the initial mass of the second experimental rock core and the adsorption amount of carbon dioxide, to obtain the adsorption amount of carbon dioxide in the first experimental rock core in the sorption trapping experiment.

In an embodiment of the present disclosure, the method for experimentation on different storage modes of carbon dioxide further comprises a method for experimentation on mineral trapping of carbon dioxide in a first experimental rock core, which is arranged after the method for experimentation on solubility trapping and comprises:

acquiring a first carbon element content in the first experimental rock core measured by the mineral analyzer before the oil saturation operation;

controlling the displacement pump to displace the carbon dioxide in the intermediate carbon dioxide container to the storage reaction device for an oil displacement operation, till the amount of carbon dioxide at the inlet end of the storage reaction device is equal to the amount of carbon dioxide at the outlet end of the storage reaction device;

acquiring the dry mass of the first experimental rock core measured by the weigher, acquiring a second carbon element content in the first experimental rock core measured by the mineral analyzer after the oil saturation operation; and performing calculations according to the initial mass of the first experimental rock core, the molecular weight of carbon dioxide, the molecular weight of carbon, the dry mass, the first carbon element content and the second carbon element content, to obtain the storage amount of carbon dioxide in the mineral trapping experiment.

In an embodiment of the present disclosure, the method for experimentation on different storage modes of carbon dioxide further comprises a method for experimentation on structural trapping, which comprises:

acquiring the injected amount of carbon dioxide and the outputted amount of carbon dioxide in the oil displacement operation; and performing calculations according to the injected amount of carbon dioxide, the outputted amount of carbon dioxide, the storage amount of carbon dioxide in the solubility trapping experiment, the storage amount of carbon dioxide in the sorption trapping experiment and the storage amount of carbon dioxide in the mineral trapping experiment, to obtain the storage amount of carbon dioxide in the structural trapping experiment.

With the above technical scheme, the combined apparatus for experimentation on different storage modes of carbon dioxide provided by the embodiments of the present disclosure has the following beneficial effects:

The combined apparatus for experimentation on different storage modes of carbon dioxide comprises a displacement device, a storage reaction device and a measuring device, wherein the displacement device comprises a displacement pump, and an intermediate water-oil container and an intermediate carbon dioxide container that are arranged in parallel, the displacement pump is connected to a first end of the parallel connection of the intermediate water-oil container and the intermediate carbon dioxide container and used for displacing a displacement medium in the intermediate water-oil container and/or the intermediate carbon dioxide container; the intermediate water-oil container is connected via the displacement pump to simulate the formation of water and oil in the strata, and the intermediate carbon dioxide container is connected via the displacement pump to simulate oil recovery in the strata by carbon dioxide storage; the inlet end of the storage reaction device is connected with a second end of the parallel connection of the intermediate water-oil container and the intermediate carbon dioxide container, and is used for storage experiments on experimental rock cores therein, so as to simulate the effect of carbon dioxide storage in the oil reservoir in the real world through the reaction of the experimental rock core with the oil-water medium and carbon dioxide; the measuring device comprises a weigher, a first pressure detector, a gas-liquid separator, a gas meter and a mineral analyzer, wherein the first pressure detector is placed in the intermediate water-oil container; after excessive carbon dioxide is injected into the intermediate water-oil container, the solubility of carbon dioxide in formation water or crude oil is calculated according to the pressure detection data detected by the first pressure detector, and the mass of the experimental rock core after a water saturation operation and an oil saturation operation can be weighed by means of the weigher, so that the data on the storage amount of carbon dioxide in the method for experimentation on solubility trapping can be obtained by using the first pressure detector and the weigher through calculation. The mineral analyzer measures a first carbon element content and a second carbon element content in the experimental rock core before and after the oil saturation operation, and the weigher can weigh the mass of the experimental rock core after the oil saturation operation, thereby the data on the storage amount of carbon dioxide in the method for experimentation on mineral trapping can be obtained by using the mineral analyzer and the weigher through calculation. The combined apparatus for experimentation on different storage modes of carbon dioxide further comprises a carbon dioxide adsorption instrument, another experimental rock core is placed in the carbon dioxide adsorption instrument for carbon dioxide adsorption, and the adsorption amount of carbon dioxide is measured, and the mass of the experimental rock core is measured by the weigher, thereby the data on the storage amount of carbon dioxide in the method for experimentation on sorption trapping can be collected by using the carbon dioxide adsorption instrument and the weigher through calculation.

The gas-liquid separator is connected to the outlet end of the storage reaction device, the gas meter is used to detect the outputted amount of carbon dioxide separated by the gas-liquid separator, and the displacement pump is used to measure the injected amount of carbon dioxide, thereby the data on the storage amount of carbon dioxide in the method for experimentation of structural trapping can be acquired by using the gas meter and the displacement pump through calculation, which is to say, the measuring device can acquire the data on the storage amount of carbon dioxide in the experimental rock core in different storage modes. Compared with the prior art, in which calculations are performed only for solubility trapping and mineral trapping and the storage experiments are performed separately with separate systems and apparatuses, the present disclosure can systematically evaluate the storage amount of carbon dioxide in different storage modes including solubility trapping, mineral trapping, sorption trapping and structural trapping by means of a single apparatus. Thus, the experimental steps and manual operations are reduced greatly, the effect and efficiency of the experiment are improved, the experimental result can reflect the real carbon dioxide storage situation, the calculation accuracy is improved, and the storage amount of carbon dioxide in different storage modes can be quantized.

Other features and advantages of the present disclosure will be further detailed in the following embodiments.

BRIEF DESCRIPTION OF THE DRAWINGS

The accompanying drawings are provided herein to facilitate understanding on the present disclosure and constitute a part of this document. They are used in conjunction with the following embodiments to explain the present disclosure, but are not intended to constitute any limitation to the present disclosure. In the figures.

| Reference Numbers | |
|---|---|
| 100 - displacement device | 101 - storage reaction device |
| 102 - measuring device | 103 - displacement pump |
| 104 - intermediate water-oil container | 105 - intermediate carbon dioxide container |
| 106 - weigher | 107 - first pressure detector |
| 108 - second pressure detector | 109 - gas meter |
| 110 - gas-liquid separator | 111 - mineral analyzer |
| 112 - formation water container | 113 - crude oil container |
| 114 - first valve | 115 - rock core holder |
| 116 - second valve | 117 - carbon dioxide adsorption instrument |
| 118 - confining pressure pump | |

EMBODIMENTS

Hereunder some embodiments of the present disclosure will be detailed with reference to the accompanying drawings. It should be understood that the embodiments described herein are only provided to describe and explain the present disclosure, but are not intended to constitute any limitation to the present disclosure.

The combined apparatus for experimentation on different storage modes of carbon dioxide according to the present disclosure will be described below with reference to the accompanying drawings.

Figure 1:
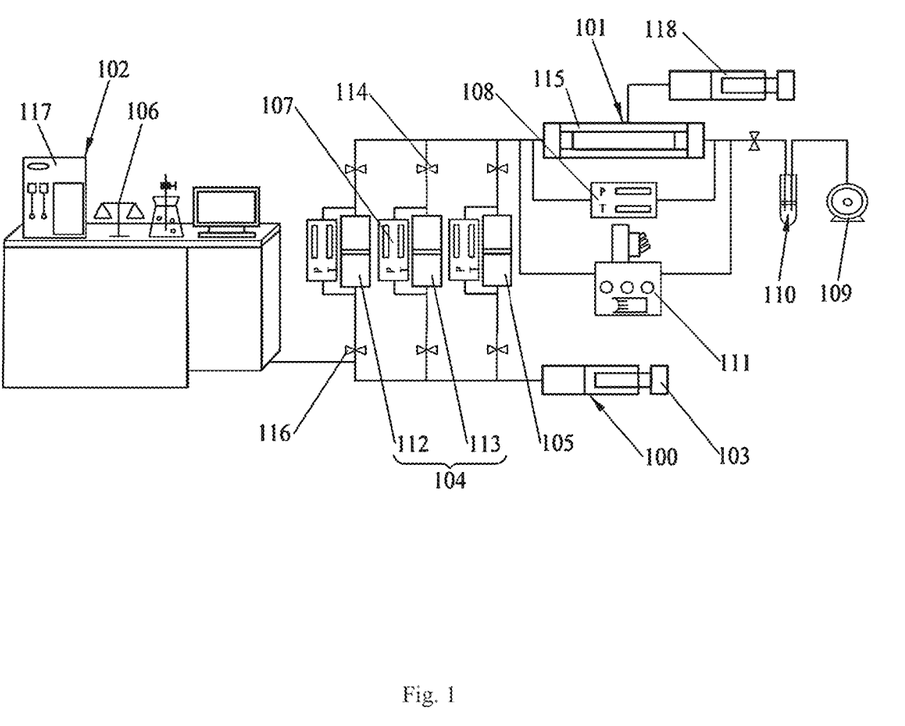
FIG. 1 is a schematic diagram of the combined apparatus for experimentation on different storage modes of carbon dioxide according to an embodiment of the present disclosure.

As shown in FIG. 1, in an embodiment of the present disclosure, a combined apparatus for experimentation on different storage modes of carbon dioxide is provided. The combined apparatus for experimentation on different storage modes of carbon dioxide comprises:

a displacement device 100 comprising a displacement pump 103, and an intermediate oil-water container 104 and an intermediate carbon dioxide container 105 that are in parallel connection, wherein the displacement pump 103 is connected to a first end of the parallel connection of the intermediate oil-water container 104 and the intermediate carbon dioxide container 105 for displacing a displacement medium in the intermediate oil-water container 104 and/or the intermediate carbon dioxide container 105;

a storage reaction device 101, which has an inlet end connected to a second end of the parallel connection of the intermediate water-oil container 104 and the intermediate carbon dioxide container 105 and is used for performing storage experiments on an experimental rock core therein; and a measuring device 102 comprising a weigher 106, a first pressure detector 107, a gas-liquid separator 110, a gas meter 109 and a mineral analyzer 111, wherein the first pressure detector 107 is arranged in the intermediate water-oil container 104, the gas-liquid separator 110 is connected to the outlet end of the storage reaction device 101, the gas meter 109 is used for detecting the gas separated by the gas-liquid separator 110, the weigher 106 is used for weighing the weight of the experimental rock core, and the mineral analyzer 111 is used for detecting the carbon content in the experimental rock core.

The intermediate water-oil container 104 is connected via the displacement pump 103 to simulate the formation of water and oil in the strata, and the intermediate carbon dioxide container 105 is connected via the displacement pump 103 to simulate oil recovery in the strata by carbon dioxide storage; the inlet end of the storage reaction device 101 is connected with a second end of the parallel connection of the intermediate water-oil container 104 and the intermediate carbon dioxide container 105, and is used for storage experiments on experimental rock cores therein, so as to simulate the effect of carbon dioxide storage in the oil reservoir in the real world through the reaction of the experimental rock core with the oil-water medium and carbon dioxide; the measuring device 102 comprises the weigher 106, the first pressure detector 107, the gas-liquid separator 110, the gas meter 109 and the mineral analyzer 111, wherein the first pressure detector 107 is placed in the intermediate water-oil container 104; after excessive carbon dioxide is injected into the intermediate water-oil container 104, the solubility of carbon dioxide in formation water or crude oil is calculated respectively according to the pressure detection data detected by the first pressure detector 107, and the mass of the experimental rock core after a water saturation operation and an oil saturation operation can be weighed by means of the weigher 106, so that the data on the storage amount of carbon dioxide in the method for experimentation on solubility trapping can be obtained by using the first pressure detector 107 and the weigher 106 through calculation. The mineral analyzer 111 measures a first carbon element content and a second carbon element content in the experimental rock core before and after the oil saturation operation, and the weigher 106 can weigh the mass of the experimental rock core after the oil saturation operation, thereby the data on the storage amount of carbon dioxide in the method for experimentation on mineral trapping can be obtained by using the mineral analyzer 111 and the weigher 106 through calculation. The gas-liquid separator 110 is connected to the outlet end of the storage reaction device 101, the gas meter 109 is used to detect the outputted amount of carbon dioxide separated by the gas-liquid separator 110, and the displacement pump 103 is used to measure the injected amount of carbon dioxide, thereby the data on the storage amount of carbon dioxide in the method for experimentation of structural trapping can be acquired by using the gas meter 109 and the displacement pump 103 through calculation, which is to say, the measuring device 102 can acquire the data on the storage amount of carbon dioxide in the experimental rock core in different storage modes. Compared with the prior art, in which calculations are performed only for solubility trapping and mineral trapping and the storage experiments are performed separately with separate systems and apparatuses, the present disclosure can systematically evaluate the storage amount of carbon dioxide in different storage modes by means of a single apparatus. Thus, the experimental steps and manual operations are reduced greatly, the effect and efficiency of the experiment are improved, the experimental result can reflect the real carbon dioxide storage situation, the calculation accuracy is improved, and the storage amount of carbon dioxide in different storage modes can be quantized.

As shown in FIG. 1, in an embodiment of the present disclosure, the intermediate water-oil container 104 comprises a formation water container 112 and a crude oil container 113, wherein the formation water container 112, the crude oil container 113 and the intermediate carbon dioxide container 105 are arranged in parallel, two first pressure detectors 107 are provided and arranged in the formation water container 112 and the crude oil container 113 respectively, the front ends of the formation water container 112, the crude oil container 113 and the intermediate carbon dioxide container 105 are provided with a first valve 114 respectively, and the rear ends of the formation water container 112, the crude oil container 113 and the intermediate carbon dioxide container 105 are provided with a second valve 116 respectively. That is to say, the two first pressure detectors 107 can detect the pressures in the formation water container 112 and the crude oil container 113 respectively. Thus, in a solubility trapping experiment, the solubility of carbon dioxide in the formation water or crude oil can be calculated according to the pressure detection data measured by the first pressure detector 107 in the formation water container 112 or the crude oil container 113 in which excessive carbon dioxide is injected. Specifically, the first valve 114 and the second valve 116 at the front end and rear end of the intermediate carbon dioxide container 105 are opened, and the first valves 114 of the formation water container 112 and the crude oil container 113 are opened, so that the displacement pump 103 can inject excessive carbon dioxide in the intermediate carbon dioxide container 105 into the formation water container 112 and the crude oil container 113 for dissolution; then, the first valves 114 of the formation water container 112 and the crude oil container 113 as well as the first valve 114 and the second valve 116 at the front end and rear end of the intermediate carbon dioxide container 105 are closed.

In addition, by controlling the opening and closing of the corresponding first valve 114 and second valve 116, any one of the formation water container 112, crude oil container 113 and intermediate carbon dioxide container 105 can communicate with the storage reaction device 101, so that the displacement pump 103 pumps the corresponding water, crude oil and carbon dioxide into the storage reaction device 101 for reacting with the experimental rock core, so as to realize detection of carbon dioxide storage.

As shown in FIG. 1, in an embodiment of the present disclosure, the storage reaction device 101 comprises a rock core holder 115 and a second pressure detector 108, wherein the experimental rock core is held in the rock core holder 115, an inlet end of the rock core holder 115 is connected to the second end of the parallel connection of the intermediate water-oil container 104 and the intermediate carbon dioxide container 105, and the gas-liquid separator 110 is connected to an outlet end of the rock core holder 115. That is to say, the rock core holder 115 plays the role of holding and protecting the experimental rock core, the second pressure detector 108 plays the role of detecting the pressure in the rock core holder 115, and the gas-liquid separator 110 is used to separate the water, oil and carbon dioxide outputted from the rock core holder 115.

As shown in FIG. 1, in an embodiment of the present disclosure, the storage reaction device 101 further comprises a confining pressure pump 118 connected to the rock core holder 115. That is to say, the confining pressure pump 118 plays the role of balancing the pressure in all parts of the rock core holder 115, so that the oil-water medium can enter the rock core holder 115 through the inlet of the rock core holder 115 and fully react with the experimental rock core, and finally can be discharged through the outlet of the rock core holder 115.

As shown in FIG. 1, in an embodiment of the present disclosure, the gas-liquid separator 110 comprises a gas-liquid separation cylinder, a gas-liquid output pipe and an exhaust pipe, wherein an inlet end of the gas-liquid output pipe is connected to the outlet end of the storage reaction device 101, an outlet end of the gas-liquid output pipe extends into the gas-liquid separation cylinder, an inlet end of the exhaust pipe extends into the gas-liquid separation cylinder, and an outlet end of the exhaust pipe is connected to the gas meter 109. That is to say, the gas-liquid mixture enters the gas-liquid separation cylinder from the outlet end of the rock core holder 115 through the gas-liquid output pipe. The gas-liquid separation cylinder is used to receive liquid crude oil and calculate the outputted amount of the crude oil, and the carbon dioxide gas is discharged into the gas meter 109 through the exhaust pipe, so that the outputted amount of carbon dioxide can be calculated conveniently and a data support is provided for calculating the storage amount of carbon dioxide.

Figure 2:
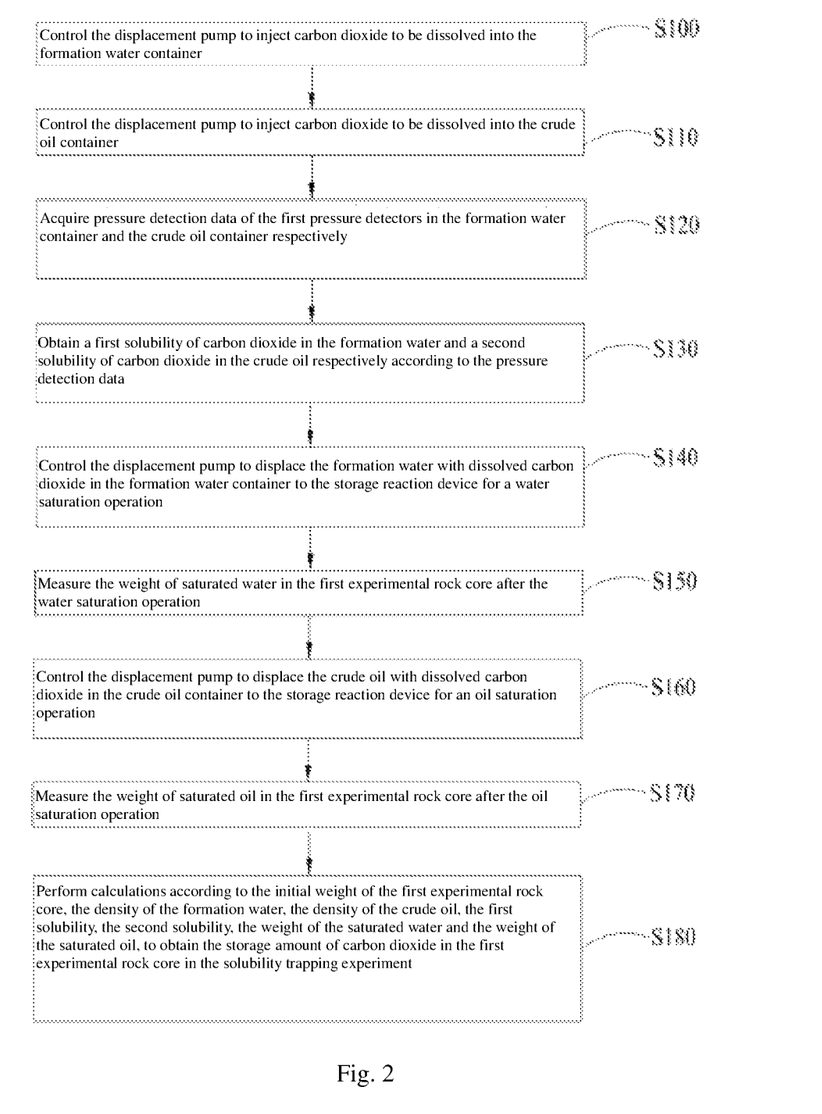
FIG. 2 is a flow chart of the method for experimentation of solubility trapping of carbon dioxide according to an embodiment of the present disclosure.

As shown in FIGS. 1 and 2, the present disclosure includes a method for experimentation on different storage modes of carbon dioxide using the above-mentioned combined apparatus for experimentation on different storage modes of carbon dioxide. The combined apparatus for experimentation on different storage modes of carbon dioxide further comprises a controller, which is in a communicative connection with the displacement pump 103 and the first pressure detector 107 respectively. The method for experimentation on different storage modes of carbon dioxide comprises a method for experimentation on solubility trapping of carbon dioxide in a first experimental rock core, which comprises the following steps:

step 100: controlling the displacement pump 103 to inject carbon dioxide to be dissolved into the formation water container 112;

step 110: controlling the displacement pump 103 to inject carbon dioxide to be dissolved into the crude oil container 113;

step 120: acquiring pressure detection data of the first pressure detectors 107 in the formation water container 113 and the crude oil container 112 respectively;

step 130: obtaining a first solubility of carbon dioxide in the formation water and a second solubility of carbon dioxide in the crude oil respectively according to the pressure detection data;

step 140: controlling the displacement pump 103 to displace the formation water with dissolved carbon dioxide in the formation water container 112 to the storage reaction device 101 for a water saturation operation;

step 150: measuring the weight of saturated water in the first experimental rock core after the water saturation operation;

step 160: controlling the displacement pump 103 to displace the crude oil with dissolved carbon dioxide in the crude oil container 113 to the storage reaction device 101 for an oil saturation operation;

step 170: measuring the weight of saturated oil in the first experimental rock core after the oil saturation operation; and step 180: performing calculations according to the initial weight of the first experimental rock core, the density of the formation water, the density of the crude oil, the first solubility, the second solubility, the weight of the saturated water and the weight of the saturated oil, to obtain the storage amount of carbon dioxide in the first experimental rock core in the solubility trapping experiment.

Specifically, in an embodiment of the present disclosure, the formation water container 112, the crude oil container 113 and the intermediate carbon dioxide container 105 are kept at the same temperature in the experiment, 100 mL formation water is injected into the formation water container 112, the displacement pump 103 is controlled by the controller to inject excessive carbon dioxide, and the first pressure detector 107 is controlled by the controller to monitor and calculate a first solubility $\rho_{dissolved\_water}$ (g/100 mL) of carbon dioxide in the formation water, 100 mL crude oil is injected into the crude oil container 113, the displacement pump 103 is controlled by the controller to inject excessive carbon dioxide, and the second pressure detector 108 is controlled by the controller to monitor and calculate a second solubility $\rho_{dissolved\_oil}$ (g/100 mL) of carbon dioxide in the crude oil. The initial mass $M_{rock\_initial}$ (g) of a first experimental rock core is measured with the weigher 106, saturated formation water is injected into the first experimental rock core in the core holder 115, and the weight $M_{saturated\_water\_in\_rock}$ (g) of saturated water in the first experimental rock core is obtained with the weigher 106: then, saturated crude oil is injected into the first experimental rock core in the core holder 115, and the weight $M_{saturated\_oil\_in\_rock}$ (g) of saturated oil in the first experimental rock core is obtained with the weigher 106; finally, the storage amount $M_{solubility}$ (g) of carbon dioxide in solubility trapping is obtained according to the known density $\rho_{water\_density}$ (g/cm$^3$) of formation water and density $\rho_{oil\_density}$ (g/cm$^3$) of crude oil. i.e., $M_{solubility} = (M_{saturated\_water\_in\_rock} - M_{rock\_initial})/\rho_{dissolved\_water} * \rho_{water\_density} + (M_{saturated\_oil\_in\_rock} - M_{saturated\_water\_in\_rock})/\rho_{dissolved\_oil} * \rho_{oil\_density}$ (g).

As shown in FIG. 1, in an embodiment of the present disclosure, the combined apparatus for experimentation on different storage modes of carbon dioxide further comprises a carbon dioxide adsorption instrument 117, which is used for performing a sorption trapping experiment on a second experimental rock core. That is to say, the carbon dioxide adsorption instrument 117 plays a role of adsorbing carbon dioxide in the second experimental rock core, and the increase in the weight of the second experimental rock core in the carbon dioxide adsorption instrument 117 after carbon dioxide adsorption is the storage amount of carbon dioxide in the second experimental rock core in sorption trapping.

Specifically, the second experimental rock core in the carbon dioxide adsorption instrument 117 is of the same type as the first experimental rock core in the core holder 115, i.e., they have the same sorption trapping feature. The theoretically sorption-trapped weight of carbon dioxide in the first experimental rock core in the core holder 115 can be obtained from a product of the weight of carbon dioxide actually adsorbed in the carbon dioxide adsorption instrument 117 multiplied by the ratio of the weight of the first experimental rock core in the rock core holder 115 to the weight of the second experimental rock core in the carbon dioxide adsorption instrument 117, and it is unnecessary to open the core holder 115 and perform carbon dioxide adsorption detection on the first experimental rock core in it to obtain more accurate data and reduce the experimental error. In that process, other storage experiments can be performed on the first experimental rock core in the core holder 115, so as to shorten the period of the entire storage experiment and improve the efficiency of the storage experiment.

Figure 3:
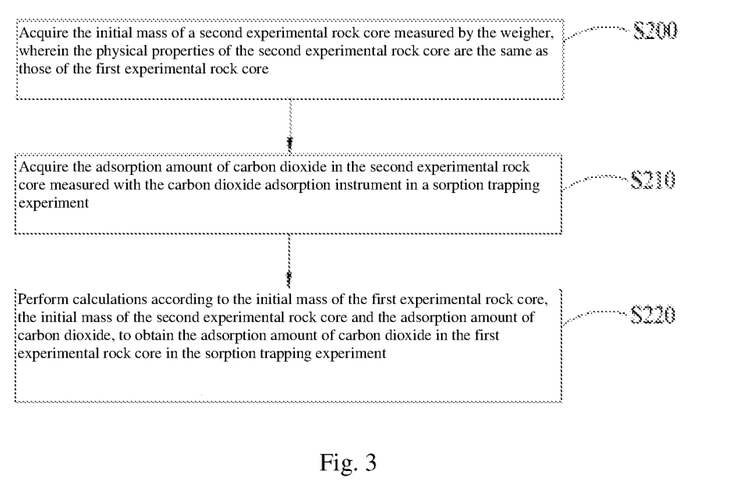
FIG. 3 is a flow chart of the method for experimentation of sorption trapping of carbon dioxide according to an embodiment of the present disclosure.

As shown in FIGS. 1 and 3, in an embodiment of the present disclosure, the controller is in a communicative connection with the carbon dioxide adsorption instrument 117, and the method for experimentation on different storage modes of carbon dioxide further comprises a method for experimentation on sorption trapping of carbon dioxide in a second experimental rock core, which comprises the following steps:

step 200: acquiring the initial mass of a second experimental rock core measured by the weigher 106, wherein the physical properties of the second experimental rock core are the same as those of the first experimental rock core;

step 210: acquiring the adsorption amount of carbon dioxide in the second experimental rock core measured with the carbon dioxide adsorption instrument 117 in a sorption trapping experiment; and step 220: performing calculations according to the initial mass of the first experimental rock core, the initial mass of the second experimental rock core and the adsorption amount of carbon dioxide, to obtain the adsorption amount of carbon dioxide in the first experimental rock core in the sorption trapping experiment.

Specifically, in an embodiment of the present disclosure, a second experimental rock core having the same physical properties as the first experimental rock core in the core holder 115 is selected, the initial mass $M_{sorption\_rock}$ (g) of the second experimental rock core is measured with the weigher 106, and the carbon dioxide adsorption instrument 117 is controlled by the controller to measure the adsorption of carbon dioxide in the second experimental rock core, so as to obtain the adsorption amount $M_{sorption\_standard}$ (g) of carbon dioxide in the second experimental rock core. Finally, the sorption-trapped amount $M_{sorption}$ of carbon dioxide is obtained according to the initial mass $M_{rock\_initial}$ (g) of the first experimental rock core in the core holder 115, i.e., $M_{sorption}=M_{rock\_initial}/M_{sorption\_rock}*M_{sorption\_standard}$ (g).

Figure 4:
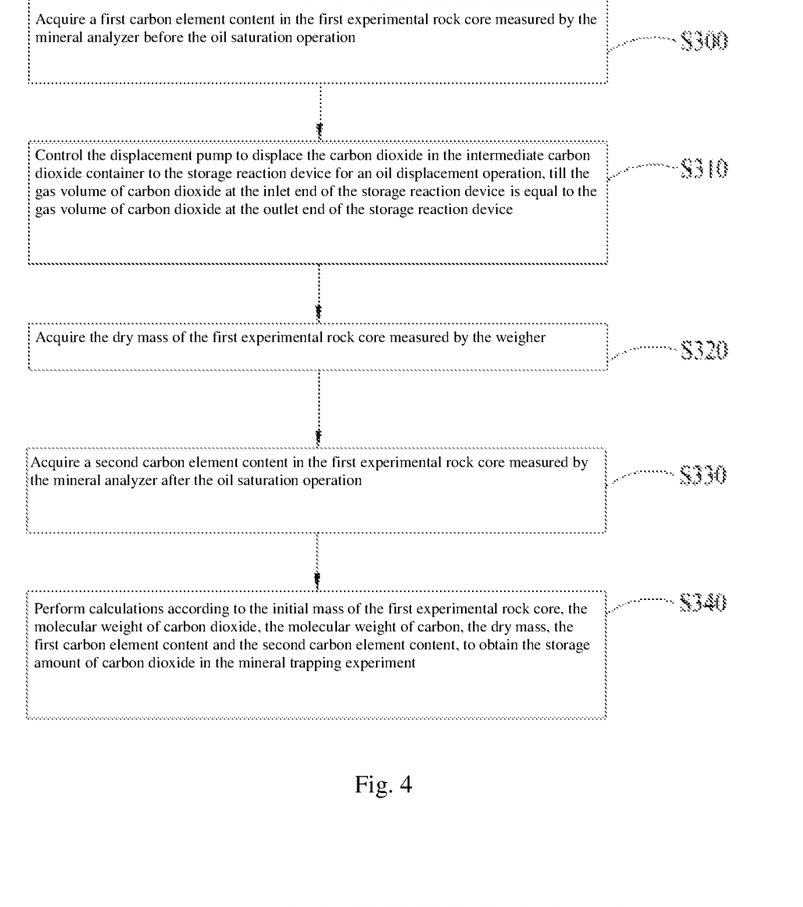
FIG. 4 is a flow chart of the method for experimentation of mineral trapping of carbon dioxide according to an embodiment of the present disclosure.

As shown in FIGS. 1 and 4, in an embodiment of the present disclosure, the controller is further in a communicative connection with a mineral analyzer 111, and the method for experimentation on different storage modes of carbon dioxide further comprises a method for experimentation on mineral trapping of carbon dioxide in a first experimental rock core, which is arranged after the method for experimentation on solubility trapping and comprises the following steps:

step 300: acquiring a first carbon element content in the first experimental rock core measured by the mineral analyzer 111 before the oil saturation operation;

step 310: controlling the displacement pump 103 to displace the carbon dioxide in the intermediate carbon dioxide container 105 to the storage reaction device 101 for an oil displacement operation, till the amount of carbon dioxide at the inlet end of the storage reaction device 101 is equal to the amount of carbon dioxide at the outlet end of the storage reaction device;

step 320: acquiring the dry mass of the first experimental rock core measured by the weigher 106;

step 330: acquiring a second carbon element content in the first experimental rock core measured by the mineral analyzer 111 after the oil saturation operation; and step 340: performing calculations according to the initial mass of the first experimental rock core, the molecular weight of carbon dioxide, the molecular weight of carbon, the dry mass, the first carbon element content and the second carbon element content, to obtain the storage amount of carbon dioxide in the mineral trapping experiment.

Specifically, in an embodiment of the present disclosure, before the storage experiment is performed, a first experimental rock core is sliced and a first carbon content $C_{initial\ \%}$ in the first experimental rock core is measured with the mineral analyzer 111; after the oil saturation operation for the solubility trapping experiment is completed, the first valve 114 and the second valve 116 on the intermediate carbon dioxide container 105 are controlled to open, so that the displacement pump 103 can be controlled by the controller to inject carbon dioxide into the rock core holder 115; after the entire oil displacement experiment of carbon dioxide is completed, the dry mass $M_{rock\_post}$ of the first experimental rock core after the injection of carbon dioxide, reaction and drying is measured with the weigher 106; then the first experimental rock core after the reaction is sliced, and a second carbon element content $C_{reaction\ \%}$ in the first experimental rock core is measured with the mineral analyzer 111; finally, the storage amount $M_{mineral}$ at of carbon dioxide in mineral trapping is obtained, i.e., $M_{mineral}=(M_{rock\_post}*C_{reaction\ \%}-M_{rock\_initial}*C_{initial})*$molecular weight of carbon dioxide/$C_{molecular\_weight}$ (g); specifically, $M_{mineral}=(M_{rock\_post}*C_{reaction\ \%}-M_{rock\_initial}*C_{initial\ \%})*3.67$ (g).

Figure 5:
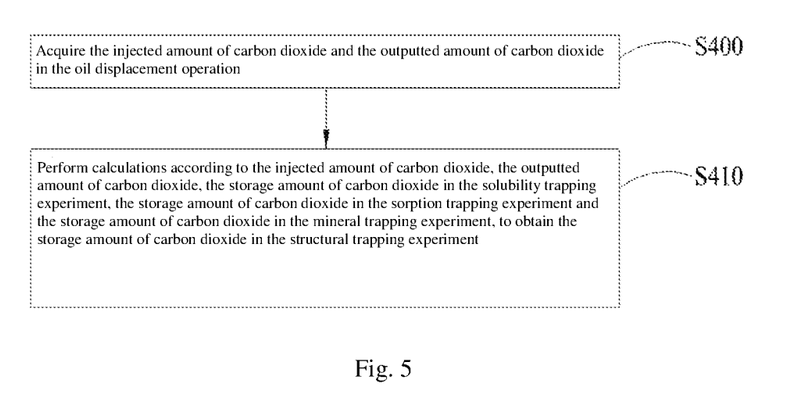
FIG. 5 is a flow chart of the method for experimentation of structural trapping of carbon dioxide according to an embodiment of the present disclosure.

As shown in FIGS. 1 and 5, in an embodiment of the present disclosure, the method for experimentation on different storage modes of carbon dioxide further comprises a method for experimentation on structural trapping, which comprises the following steps:

step 400: acquiring the injected amount of carbon dioxide and the outputted amount of carbon dioxide in the oil displacement operation; and step 410: performing calculations according to the injected amount of carbon dioxide, the outputted amount of carbon dioxide, the storage amount of carbon dioxide in the solubility trapping experiment, the storage amount of carbon dioxide in the sorption trapping experiment and the storage amount of carbon dioxide in the mineral trapping experiment, to obtain the storage amount of carbon dioxide in the structural trapping experiment.

Specifically, in the mineral trapping experiment, the first valve 114 and the second valve 116 on the intermediate carbon dioxide container 105 are controlled to open, so that the displacement pump 103 can be controlled by the controller to inject excessive carbon dioxide into the inlet end of the rock core holder 115, till there is no crude oil output at the outlet end of the rock core holder 115 and the amount of carbon dioxide at the inlet end of the core holder 115 is equal to the amount of carbon dioxide at the outlet end within one hour, i.e., the amount of carbon dioxide pumped by the displacement pump 103 is equal to the amount of carbon dioxide measured by the gas meter 109. In the entire experiment, the amount of carbon dioxide injected by displacement pump 103 is $M_{injection}$ (g), and the outputted amount of carbon dioxide collected by the gas meter 109 is $M_{output}$ (g); thus, the final storage amount of carbon dioxide in structural trapping is $M_{structure}=M_{injection}-M_{output}-M_{solubility}-M_{sorption}-M_{mineral}$ (g).

Specifically, after the storage amount of carbon dioxide in each of the four storage modes is obtained, an optimal proportionality coefficient of carbon dioxide storage in the four storage experiments can be determined according to the storage amount of carbon dioxide in the solubility trapping experiment, the storage amount of carbon dioxide in the sorption trapping experiment, the storage amount of carbon dioxide in the mineral trapping experiment and the storage amount of carbon dioxide in the structural trapping experiment, so that the four storage modes can be utilized optimally for carbon dioxide storage to the greatest extent.

In the description herein, it should be understood that the terms "first" and "second" are used only for a descriptive purpose, but shall not be interpreted as indicating or implying relative importance or implicitly indicating the quantity of the indicated technical features. Hence, a feature defined by "first" or "second" may explicitly or implicitly comprise at least one such feature. In the description of the present disclosure, "a plurality of" means at least two, such as two or more, etc., unless otherwise specified explicitly.

In the present disclosure, unless otherwise specified and defined explicitly, the terms "install", "connect", "fix", etc. shall be interpreted in their general meanings. For example, the connection may be a fixed connection, a detachable connection, or an integral connection; may be a mechanical connection or an electrical connection or in communication with each other, may be a direct connection or an indirect connection via an intermediate medium, or internal communication or interactive relation between two elements. Those having ordinary skills in the art may interpret the specific meanings of the terms in the present disclosure in their context.

In the description of the present disclosure, the expressions of reference terms "an embodiment", "some embodiments", "an example", "a specific example", or "some examples" mean that the specific features, structures, materials or characteristics described in those embodiments or examples are included in at least one embodiment or example of the present disclosure. In this document, the exemplary expression of the above terms may not necessarily refer to the same embodiment or example. Moreover, the specific features, structures, materials, or characteristics described can be combined appropriately in any one or more embodiments or examples. Furthermore, those skilled in the art may combine or assemble different embodiments or examples and features in different embodiments or examples described herein, provided that there is no conflict among them.

While the present disclosure is illustrated and described above in embodiments, it should be understood that the embodiments are exemplary only and shall not be deemed as constituting any limitation to the present disclosure. Those skilled in the art can make variations, modifications, and replacements to the embodiments within the scope of the present disclosure.

The invention claimed is:

1. A method for experimentation on different storage modes of carbon dioxide using a combined apparatus, wherein the combined apparatus comprises:

a displacement device comprising a displacement pump, and a water-oil intermediate container and a carbon dioxide intermediate container arranged in parallel, wherein the displacement pump is connected with a first end of a parallel connection of the water-oil intermediate container and the carbon dioxide intermediate container for displacing a displacement medium in the water-oil intermediate container and/or the carbon dioxide intermediate container; the water-oil intermediate container comprises a formation water container and a crude oil container;

a storage reaction device, wherein an inlet end of the storage reaction device is connected with a second end of the parallel connection of the water-oil intermediate container and the carbon dioxide intermediate container for performing storage experiments on an experimental rock core arranged inside; and a measuring device comprising a weigher, first pressure detectors, a gas-liquid separator, a gas meter and a mineral analyzer, wherein the first pressure detectors are placed in the water-oil intermediate container, the gas-liquid separator is connected with an outlet end of the storage reaction device, the gas meter is used to detect a gas amount separated by the gas-liquid separator, the weigher is used to weigh a weight of the experimental rock core, and the mineral analyzer is used to detect a carbon element content in the experimental rock core;

wherein the method for experimentation on different storage modes of carbon dioxide comprises a method for a dissolve and storage experiment on a first experimental rock core, and the method for the dissolve and storage experiment comprises:

controlling the displacement pump to inject carbon dioxide to be dissolved into the formation water container;

controlling the displacement pump to inject the carbon dioxide to be dissolved into the crude oil container;

obtaining pressure detection data of the first pressure detectors in the formation water container and the crude oil container respectively;

obtaining a first solubility of carbon dioxide in formation water and a second solubility of carbon dioxide in crude oil respectively according to the pressure detection data;

controlling the displacement pump to displace formation water with dissolved carbon dioxide in the formation water container to the storage reaction device for a saturated water operation;

measuring a saturated water weight in the first experimental rock core after the saturated water operation;

controlling the displacement pump to displace crude oil with dissolved carbon dioxide in the crude oil container to the storage reaction device for a saturated oil operation;

measuring a saturated oil weight in the first experimental rock core after the saturated oil operation; and performing calculations according to an initial weight, a formation water density, a crude oil density, the first solubility, the second solubility, the saturated water weight and the saturated oil weight of the first experimental rock core, to obtain a carbon dioxide storage amount in the first experimental rock core in the dissolve and storage experiment.

2. The method for experimentation on different storage modes of carbon dioxide according to claim 1, wherein the formation water container, the crude oil container and the carbon dioxide intermediate container are arranged in parallel, a number of the first pressure detectors is two, and two the first pressure detectors are arranged in the formation water container and the crude oil container respectively, front ends of the formation water container, the crude oil container and the carbon dioxide intermediate container are provided with a first valve respectively, and each of rear ends of the formation water container, the crude oil container and the carbon dioxide intermediate container is provided with a second valve.

3. The method for experimentation on different storage modes of carbon dioxide according to claim 1, wherein the storage reaction device comprises a rock core holder and a second pressure detector, wherein the rock core holder is arranged inside the experimental rock core, an inlet end is connected with the second end of the parallel connection of the water-oil intermediate container and the carbon dioxide intermediate container, and the gas-liquid separator is connected with an outlet end of the rock core holder.

4. The method for experimentation on different storage modes of carbon dioxide according to claim 3, wherein the storage reaction device further comprises a confining pressure pump connected with the rock core holder.

5. The method for experimentation on different storage modes of carbon dioxide according to claim 1, wherein the gas-liquid separator comprises a gas-liquid separation cylinder, a gas-liquid output pipe and an exhaust pipe, an inlet end of the gas-liquid output pipe is connected with the outlet end of the storage reaction device, an outlet end of the gas-liquid output pipe extends into the gas-liquid separation cylinder, an inlet end of the exhaust pipe extends into the gas-liquid separation cylinder, and an outlet end of the exhaust pipe is connected to the gas meter.

6. The method for experimentation on different storage modes of carbon dioxide according to claim 1, wherein the combined apparatus for experimentation on different storage modes of carbon dioxide further comprises a carbon dioxide adsorption instrument, the carbon dioxide adsorption instrument is used for performing a binding and storage experiment on a second experimental rock core.

7. The method for experimentation on different storage modes of carbon dioxide according to claim 6, wherein the method for experimentation on different storage modes of carbon dioxide further comprises a method for the binding and storage experiment on the second experimental rock core, the method for the binding and storage experiment comprises:
    obtaining an initial weight of the second experimental rock core measured by the weigher, wherein physical properties of the second experimental rock core are same as those of the first experimental rock core;
    obtaining a carbon dioxide adsorption amount in the second experimental rock core measured with the carbon dioxide adsorption instrument in the binding and storage experiment; and
    performing calculations according to the initial weight of the first experimental rock core, the initial weight of the second experimental rock core and the carbon dioxide adsorption amount, to obtain a carbon dioxide storage amount in the first experimental rock core in the binding and storage experiment.

8. The method for experimentation on different storage modes of carbon dioxide according to claim 7, wherein the method for experimentation on different storage modes of carbon dioxide further comprises a method for a mineralization and storage experiment on the first experimental rock core, the method for the mineralization and storage experiment is performed after the method for the binding and storage experiment and comprises:
    obtaining a first carbon element content in the first experimental rock core measured by the mineral analyzer before the saturated oil operation;
    controlling the displacement pump to displace the carbon dioxide in the carbon dioxide intermediate container to the storage reaction device for an oil displacement operation, till carbon dioxide amounts at the inlet end and the outlet end of the storage reaction device are equal;
    obtaining a dry weight of the first experimental rock core measured by the weigher;
    obtaining a second carbon element content in the first experimental rock core measured by the mineral analyzer after the saturated oil operation; and
    performing calculations according to the initial weight, a carbon dioxide molecular weight, a carbon molecular weight, the dry weight, the first carbon element content and the second carbon element content of the first experimental rock core, to obtain a carbon dioxide storage amount in the mineralization and storage experiment.

9. The method for experimentation on different storage modes of carbon dioxide according to claim 8, wherein the method for experimentation on different storage modes of carbon dioxide further comprises a method for a construction and storage experiment, the method for the construction and storage experiment comprises:
    obtaining a carbon dioxide injected amount and a carbon dioxide outputted amount in the oil displacement operation; and
    performing calculations according to the carbon dioxide injected amount, the carbon dioxide outputted amount, the carbon dioxide storage amount in the dissolve and storage experiment, the carbon dioxide storage amount in the binding and storage experiment and the carbon dioxide storage amount in the mineralization and storage experiment, to obtain a carbon dioxide storage amount in the construction and storage experiment.

* * * * *